United States Patent [19]

Scrivens et al.

[11] Patent Number: 5,731,474
[45] Date of Patent: Mar. 24, 1998

[54] METHOD OF MAKING ACETALS

[75] Inventors: Walter A. Scrivens, Newberry; Joseph M. Salley, Spartanburg, both of S.C.

[73] Assignee: Milliken Research Corporation, Spartanburg, S.C.

[21] Appl. No.: 792,518

[22] Filed: Jan. 31, 1997

[51] Int. Cl.$^6$ .................................................. C07C 43/307
[52] U.S. Cl. ............................................ 568/592; 568/593
[58] Field of Search .................................. 568/592, 593

[56] References Cited

U.S. PATENT DOCUMENTS

| | | | |
|---|---|---|---|
| 3,721,682 | 3/1973 | Murai et al. | 260/340.7 |
| 4,429,140 | 1/1984 | Murai et al. | 549/370 |
| 4,562,265 | 12/1985 | Machell | 549/364 |
| 4,902,807 | 2/1990 | Kobayashi et al. | 549/364 |

FOREIGN PATENT DOCUMENTS 0 497 976 B1  9/1996  European Pat. Off. ........... C07D 4/93

OTHER PUBLICATIONS

Kirk–Othmer; Encyclopedia of Chemical Technology; Third Edition; vol. 11; pp. 921–941 1980.

*Primary Examiner*—Gary Geist
*Assistant Examiner*—Sreeni Padmanabhan
*Attorney, Agent, or Firm*—Terry T. Moyer; Timothy J. Monahan

[57] ABSTRACT

A method of making acetals is provided by condensing an aromatic aldehyde and a polyhydric alcohol having five or more hydroxyl groups in the presence of an acid catalyst, a hydrophobic organic liquid medium and a processing agent selected from dihydric, trihydric and tetrahydric alcohols.

20 Claims, No Drawings

METHOD OF MAKING ACETALS

BACKGROUND OF THE INVENTION

This invention relates to a process for making diacetals, such as dibenzylidene sorbitol acetal, by the condensation reaction of an aromatic aldehyde and a polyhydric alcohol.

Dibenzylidene sorbitol acetals "DBS", substituted DBS, such as can be made with alkyl substituted aromatic aldehydes, and related acetals have found utility as nucleating agents clarifying agents, gelling agents, processing aids and strength modifiers in polyolefin resins, polyester resins, deodorant, and antiperspirant compositions, hydrocarbon fuels, waste liquids, especially those containing organic impurities and paint.

The DBS type compounds are typically prepared by the condensation reaction of two moles of an aromatic aldehyde with one mole of a polyhydric alcohol, such as xylitol or sorbitol. Examples of suitable processes may be found in Murai et al., U.S. Pat. No. 3,721,682; Murai et al., U.S. Pat. No. 4,429,140; Machell, U.S. Pat. No. 4,562,265; and Kobayashi et al., U.S. 4,902,807. The drawbacks of the aforementioned processes are that they do not lead to high yields, high purity, require specialized equipment or are otherwise not economically desirable.

More recently, EP 0 497 976 B1 (New Japan Chemical Co.) disclosed a method of producing acetals involving multiple additions and removal of a lower alcohol, such as methanol from the reaction mixture. Despite improvements in purity and yield, the process requires the use of large volumes of the lower alcohol, which must be purified and recycled back into the system. Additionally, the multiple additions and removal of methanol tend to increase the overall cycle time of the process.

SUMMARY OF THE INVENTION

Therefore, the objects of the invention are to avoid the aforementioned drawbacks and to provide a process for making acetals characterized by high yield and purity, a product free from discoloration, minimal use of solvents and a relatively high production rate.

Accordingly, a method of making acetals is provided in which an aromatic aldehyde, a polyhydric alcohol having five or more hydroxyl groups, an acid catalyst, a hydrophobic organic liquid medium and a processing agent selected from dihydric, trihydric and tetrahydric alcohols are combined in a reaction mixture. The reaction mixture is heated to drive the condensation reaction between the aromatic aldehyde and the polyhydric alcohol. Preferably, the condensation reaction is conducted at a temperature below the boiling temperature of the processing agent. Optionally, a lower alcohol, such as $C_{1-4}$ monohydric alcohols or furfuryl alcohol may be added to the reaction mixture before and/or during the condensation reaction period.

DETAILED DESCRIPTION OF THE INVENTION

Without limiting the scope of the invention, the preferred embodiments and features are hereinafter set forth. Unless otherwise indicated, all parts and percentages are by weight and conditions are ambient, i.e. one atmosphere of pressure and 25° C.

All of the United States patents cited in the specifications are hereby incorporated by reference.

The diacetals of the present invention are made by the condensation reaction between two moles of an aromatic aldehyde and one mole of a polyhydric alcohol. The aldehyde and polyhydric alcohol are generally provided in the reaction mixture in a ratio from 1:1 to 4:1, preferably 1.5:1 to 2.5:1, respectively.

The aromatic aldehydes are single or fused double ring aldehydes having at least one unsaturated hydrocarbon ring, and include benzaldehyde, naphthaldehyde, indan aldehyde and tetrahydronaphthaldehyde (tetralin aldehyde). The aromatic aldehydes may be unsubstituted or have from one to five substituent groups selected from $C_{1-4}$ alkyl, $C_{1-4}$ alkoxy, hydroxy, halogen, $C_{1-6}$ alkylthio, $C_{1-6}$ alkylsulfoxy, $C_{3-5}$ alkylene forming a carbocyclic ring with adjacent carbon atoms on an unsaturated hydrocarbon ring, carboxyl, $(C_{1-20}$ alkyloxy)carbonyl, $(C_{1-20}$ alkyloxy)ethyloxycarbonyl, $(C_{1-12}$ alkyl)phenyl, halogenated phenyl, $(C_{1-12}$ alkoxy)phenyl, $(C_{1-12}$ alkyloxy)ethyloxyethyloxycarbonyl and $(C_{1-12}$ alkyloxy)ethyloxyethyloxyethyloxycarbonyl groups. Preferably, the aromatic aldehyde is selected from unsubstituted benzaldehyde, benzaldehyde having from one to three substituent groups selected from $C_{1-4}$ alkyl, halogen and $C_{3-5}$ alkylene forming a carbocyclic ring with adjacent carbon atoms on an unsaturated hydrocarbon ring, including p-methyl, p-ethyl, 2,4-dimethyl, 3,4-dimethyl and 2,4,5-trimethyl benzaldehyde, 5-indan aldehyde and 5', 6', 7', 8'-tetrahydro-2-naphthaldehyde. Preferred aromatic aldehydes are represented by the formula:

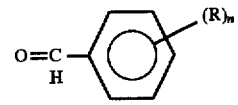

wherein n is 0, 1, 2 or 3, and R is $C_{1-4}$ alkyl, halogen, or a three or four membered alkylene group forming a carbocyclic ring with adjacent atoms of the unsaturated parent ring.

Mixtures of the aromatic aldehydes may be provided and will result in a distribution of diacetals having the same or different aromatic components, referred to as symmetric and asymmetric diacetals, respectively. The aromatic aldehydes typically react with the polyhydric alcohol to form acetals in the 1:3 and 2:4 positions. Also within the scope of the present invention are triacetals formed by the condensation of three moles of an aromatic aldehyde and one mole of a polyhydric alcohol having six or more hydroxyl groups. The triacetals are typically formed at the 1:3, 2:4 and 5:6 positions of the alcohol.

The polyhydric alcohols have five or more hydroxyl groups. The sugar alcohols represented by the formula $HOCH_2(CHOH)_n CH_2OH$, where n=3–5, have been found to be especially useful. Preferably, the polyhydric alcohol is a pentahydric or hexahydric alcohol, most preferably xylitol or sorbitol.

The polyhydric alcohol can be added to the reaction mixture as a solid, molten liquid, or as an aqueous solution. Preferably, the polyhydric alcohol is concentrated to a syrup by the azeotropic removal of water with a hydrophobic solvent, such as cyclohexane, prior to addition.

The condensation reaction is conducted in a hydrophobic organic liquid medium, in the presence of an acid catalyst. The hydrophobic organic liquid preferably has a boiling point between 40°–200° C. Suitable organic liquids include benzene, toluene, xylene, cyclohexane, which may have from one to three $C_{1-4}$ alkyl substituents, and $C_{6-16}$ saturated or unsaturated aliphatic hydrocarbons. Preferably the hydrophobic organic liquid is cyclohexane or substituted cyclohexane.

The ratio of reactants (aromatic aldehydes and polyhydric alcohols) to the hydrophobic organic liquid medium can vary over a wide range within the scope of the present invention. Those skilled in the art will recognize that if the reaction mixture is overly dilute, the reaction rate will be slowed and equipment will be under-utilized, and if the reaction mixture is overly concentrated, it will become viscous and difficult to mix without specialized equipment and the yield and quality of product will suffer. In general, the reactants will constitute from about 5 to 90 wt % of the total mixture of reactants, hydrophobic organic solvent and catalyst; most preferably the reactants will constitute from 5 to 30 wt % of the mixture.

The acid catalyst used in the reaction is preferably selected from Brönsted acids, such as sulfuric, phosphoric, hydrochloric, or $C_{1-18}$ alkylbenzenesulfonic acids, especially p-toluenesulfonic acids and m-toluenesulfonic acids, or napthalenesulfonic acids.

The amount of acid required to catalyze the condensation reaction may be readily determined experimentally for each set of reaction conditions. In general, the catalyst is provided at a level of about 0.05 to 10 parts by weight, preferably 0.1 to 5 parts by weight per 100 parts by weight of the reactants (aromatic aldehydes and polyhydric alcohols).

The acid catalyst can be added either in its pure form or as a solution in an acceptable solvent, for example in the hydrophobic organic liquid or a lower alcohol. The catalyst may be charged to the reactor initially, added after the reactants have been heated or added intermittently during the condensation reaction.

In addition to the aromatic aldehyde, polyhydric alcohol, hydrophobic organic liquid medium and acid catalyst, the reaction mixture includes a processing agent selected from dihydric, trihydric and tetrahydric alcohols. The processing agent is preferably a liquid at ambient temperature and has a molecular weight of 1,000 or less. The di- and tri-hydric alcohols are preferable, especially those which are water soluble. Examples of suitable processing agents include aliphatic diols and triols, in particular, glycerol, ethylene glycol and propylene glycol. The processing agents are present in the reaction mixture at a level of about 0.5 or greater parts by weight per 100 parts by weight of the reactants, preferably 1 to 25 parts by weight per 100 parts by weight of the reactants, most preferably 2 to 15 parts by weight per 100 parts by weight of the reactants.

The reaction mixture may optionally include a lower alcohol characterized as a monohydric alcohol having from 1 to 6 carbon atoms. For example, the lower alcohol may be selected from $C_{1-4}$ aliphatic alcohols, including, methanol, ethanol, n-propanol, isopropanol, butanol and allyl alcohol, or furfuryl alcohol.

The lower alcohol may be charged to the reactor in the amount of 20 to 500 parts by weight, preferably, 50 to 200 parts by weight, per 100 parts by weight of the reactants. The lower alcohol may be charged at the beginning of the condensation reaction and/or one or more times intermittently during the reaction, after a portion of the lower alcohol is removed by distillation. The addition and withdrawal of the lower alcohol may be repeated several times, although it is not necessary to achieve a high yield and purity, and diminishing returns are soon realized.

The condensation reaction is preferably conducted as a batch reaction, but may also be run as a continuous reaction. By way of example, a reactor equipped with a condenser, thermometer, gas inlet, stirrer, and Dean-Stark trap can be used, so that the aqueous or lower alcohol component of the condensate can be removed from the reaction mixture and the hydrophobic organic liquid recycled. The reaction is preferably conducted under nitrogen or other inert atmosphere to avoid color formation and for safety. The reaction mixture may include additional components without deviating from the scope of the invention. For example, the initial charge to the reactor may include 1% or more of the diacetal produced from a prior production batch.

The condensation reaction is initiated by heating the reaction mixture above ambient temperature. The reaction temperature may vary, depending on the choice of hydrophobic organic liquid medium, the presence and identity of the lower alcohol, the identity of the reactants and their relative concentrations in the reaction mixture. Preferably, the reaction is heated to about 40° to 200° C. Generally, the condensation reaction is ultimately conducted at a temperature approaching or at the reflux temperature of the hydrophobic organic liquid. For example, when the hydrophobic organic liquid employed is cyclohexane, the reaction temperature is preferably between 75° and 81 ° C.

The reaction time will vary depending upon the identity of the aromatic aldehyde and other components of the reaction mixture, the reaction temperature and the type of reactor, for example batch versus continuous reactor. Generally, batch reactions are substantially complete in 2 to 16 hours.

Upon completion of the condensation reaction, the reaction mixture is worked up by neutralization with a base such as alkali or alkaline metal, hydroxides or salts, e.g. potassium hydroxide, sodium hydroxide, sodium bicarbonate, ammonia or primary, secondary or tertiary amine. The base may be added in the form of an aqueous, alcoholic or hydrocarbon solution. Next, the reaction mixture is washed one or more times, preferably with hot water or alcohol, and surfactants, such as a nonionic surfactant. The remaining organic solvents can be removed by distillation, leaving an aqueous slurry. The product may then be filtered and dried by conventional methods.

The invention may be further understood by reference to the following examples, but is not intended to be limited thereby.

Color Evaluation

In the following examples, the color was evaluated by the following method. Into a 250 mL flask, were charged 0.5 g of product, 1.0 g of bis(trimethylsilyi)acetamide, and 39 g of dimethylformamide. The flask was stoppered and sonicated for 30 minutes until the contents completely dissolved. The solution was filtered and transferred into a No. 611-T Nessler sample tube; a No. 611-T Nessler tube cap was placed on the tube. A reference solution of water was prepared in the reference tube, and the color of the sample was measured relative to an APHA standard using a Oberco-Hellige Aqua Tester. The measured values range from zero and above, with water being assigned a value of zero. The lower the measured value, the less color observed.

EXAMPLE 1

A two-liter four-necked reactor was equipped with a thermometer, stirrer, nitrogen gas inlet, and condenser with a Dean Stark trap. Into the reactor was charged 38.15 g of 100% sorbitol, 56.00 g 3,4-dimethylbenzaldehyde, 4.0 g p-toluenesulfonic acid, 900 ml cyclohexane, 70 ml methanol, and 20 g glycerine. The reaction was brought to reflux for four hours during which time methanol and water were collected in the Dean Stark trap. The reaction was cooled, neutralized with a solution of 4 g KOH/20 mL methanol, and washed with hot water. The remaining solvents were removed, and the bis(3,4-dimethylbenzylidene) sorbitol acetal product was dried. The results of the process were as follows:

Product Yield: 57%
Purity: 90%
Color: 55

EXAMPLE 2 (Comparative)

A diacetal product was prepared in the same manner as in Example 1, except that no glycerine was used. The results of the process were as follows:

Product Yield: 39%
Purity: 67%
Color: 95

EXAMPLE 3

A diacetal was prepared in the same manner as Example 1, except that 10 g of propylene glycol was used in place of the glycerine. The results of the process were as follows:

Product Yield: 66%
Purity: 97%
Color: 55

The method of the present invention has the following features and advantages:

very low product discoloration;

relatively high yield in purity;

can be conducted at ambient pressure;

minimizes lower alcohol requirements;

can be conducted at relatively high temperatures;

increased reaction rate and decrease cycle time; and conducted in a hydrophobic organic liquid medium.

There are, of course, many alternative embodiments and modifications of the invention which are intended to be included within the scope of the following claims.

What we claim is:

1. A method of making an acetal product, comprising the steps of:

(a) providing a reaction mixture of an aromatic aldehyde, a polyhydric alcohol having five or more hydroxyl groups, an acid catalyst, a hydrophobic organic liquid medium, and a processing agent selected from the group consisting of dihydric, trihydric and tetrahydric alcohols; and (b) heating the reaction mixture to affect a condensation reaction between the aromatic aldehyde and the polyhydric alcohol to form a diacetal, whereby the temperature is less than a boiling temperature of the processing agent and the processing agent is present in the reaction mixture during the condensation reaction.

2. The method of claim 1 wherein the polyhydric alcohol is selected from the group consisting of pentahydric and hexahydric alcohols; and the processing agent is selected from the group consisting of water soluble, dihydric and trihydric alcohols.

3. The method of claim 2 wherein the hydrophobic organic liquid is selected from the group consisting of benzene, toluene, xylene, cyclohexane which may have from one to three $C_{1-4}$ alkyl groups, and $C_{6-16}$ saturated, aliphatic hydrocarbons.

4. The method of claim 3 wherein the aromatic aldehyde is selected from the group consisting of compounds of the formula:

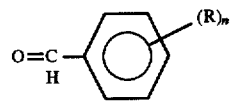

wherein n is 0, 1, 2 or 3, and R is $C_{1-4}$ alkyl, halogen, or a three or four membered alkylene group forming a carbocyclic ring with adjacent atoms of the unsaturated parent ring.

5. The method of claim 4 wherein the reaction mixture further comprises a lower alcohol selected from the group consisting of $C_{1-4}$ aliphatic monohydric alcohols and furfuryl alcohol.

6. The method of claim 1 wherein the polyhydric alcohol is selected from the group consisting of xylitol and sorbitol; and the processing agent is selected from the group consisting of glycerol, propylene glycol and ethylene glycol.

7. The method of claim 6, wherein the processing agent is present in a concentration of 0.5 parts by weight or greater per 100 parts by weight of the aromatic aldehyde and polyhydric alcohol.

8. The method of claim 7 wherein the aromatic aldehyde is selected from the group consisting of compounds of the formula:

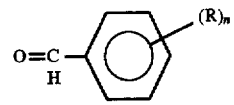

wherein n is 0, 1, 2 or 3, and R is $C_{1-4}$ alkyl, halogen, or a three or four membered alkylene group forming a carbocyclic ring with adjacent atoms of the unsaturated parent ring.

9. The method of claim 7 wherein the reaction mixture further comprises a lower alcohol selected from the group consisting of $C_{1-4}$ aliphatic monohydric alcohols and furfuryl alcohol.

10. The method of claim 2 wherein the processing agent is present in a concentration of from 1 to 25 parts by weight per 100 parts by weight of the aromatic aldehyde and polyhydric alcohol.

11. A method of making a diacetal product, comprising the steps of:

(a) providing a reaction mixture of an aromatic aldehyde, sorbitol, an acid catalyst, a hydrophobic organic liquid medium, a lower alcohol selected from the group consisting of methanol, ethanol, propanol, isopropanol and butanol, and a processing agent selected from the group consisting of glycerol, propylene glycol and ethylene glycol; and (b) heating the reaction mixture to affect a condensation reaction between the aromatic aldehyde and sorbitol to form a diacetal, whereby the temperature is less than a boiling temperature of the processing agent and the processing agent is present in the reaction mixture during the condensation reaction.

12. The method of claim 11 wherein the processing agent is present in a concentration of 2 to 15 parts by weight per 100 parts by weight of the aromatic aldehyde and sorbitol.

13. The method of claim 12 wherein the aromatic aldehyde is selected from the group consisting of compounds of the formula:

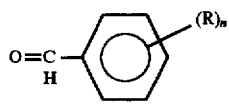

wherein n is 0, 1, 2 or 3, and R is $C_{1-4}$ alkyl, halogen, or a three or four membered alkylene group forming a carbocyclic ring with adjacent atoms of the unsaturated parent ring, and the hydrophobic organic liquid is selected from the group consisting of benzene, toluene, xylene, cyclohexane and $C_{6-16}$ saturated, aliphatic hydrocarbons.

14. A reaction mixture comprising an aromatic aldehyde, a polyhydric alcohol having five or more hydroxyl groups, an acid catalyst, a hydrophobic organic liquid medium, and a processing agent selected from the group consisting of dihydric, trihydric and tetrahydric alcohols, wherein the processing agent is present in a concentration of 0.5 parts by weight or greater per 100 parts by weight of the aromatic aldehyde and polyhydric alcohol.

15. The reaction mixture of claim 14 wherein the processing agent is present in a concentration of 1 to 25 parts by weight per 100 parts by weight of the aromatic aldehyde and polyhydric alcohol.

16. The reaction mixture of claim 15 wherein the processing agent is selected from the group consisting of glycerol, propylene glycol and ethylene glycol.

17. The reaction mixture of claim 15 wherein the processing agent is selected from the group consisting of water soluble, dihydric and trihydric alcohols.

18. The reaction mixture of claim 17 wherein the aromatic aldehyde is selected from the group consisting of benzaldehyde, naphthaldehyde, indan aldehyde and tetralin aldehyde, which may be unsubstituted or have one to three substituent groups selected from the group consisting of $C_{1-4}$ alkyl and halogen.

19. The reaction mixture of claim 18 further comprising a lower alcohol selected from the group consisting of methanol, ethanol, propanol, isopropanol and butanol.

20. The reaction mixture of claim 18 wherein the polyhydric alcohol is xylitol or sorbitol, the hydrophobic organic liquid is selected from the group consisting of benzene, toluene, xylene, cyclohexane and $C_{6-16}$ saturated, aliphatic hydrocarbons, the processing agent is selected from the group consisting of glycerol, propylene glycol and ethylene glycol, and the aromatic aldehyde and polyhydric alcohol are present in a ratio of from 1:1 to 4:1, respectively.

\* \* \* \* \*